United States Patent
Goldwasser et al.

(10) Patent No.: US 7,216,113 B1
(45) Date of Patent: May 8, 2007

(54) REMOTE EXECUTION OF MATERIALS LIBRARY DESIGNS

(75) Inventors: Isy Goldwasser, Palo Alto, CA (US); David R. Dorsett, Jr., Pleasanton, CA (US); Jere D. Fellmann, Livermore, CA (US)

(73) Assignee: Symyx Technologies, Inc., Santa Clara, CA (US)

( * ) Notice: Subject to any disclaimer, the term of this patent is extended or adjusted under 35 U.S.C. 154(b) by 397 days.

(21) Appl. No.: 10/043,515

(22) Filed: Mar. 26, 2001

Related U.S. Application Data

(60) Provisional application No. 60/191,783, filed on Mar. 24, 2000.

(51) Int. Cl.
*G06N 5/00* (2006.01)

(52) U.S. Cl. .............................. 706/47; 706/50; 706/62

(58) Field of Classification Search .................. 706/47, 706/13, 19, 23, 48; 702/19, 27, 32, 22, 84, 702/81, 30; 703/6, 11–13; 435/7.1; 422/130, 422/138, 198; 436/37, 171, 8; 374/20; 356/364, 356/337, 367, 445; 73/61.52; 502/104; 427/8; 250/288

See application file for complete search history.

(56) References Cited

U.S. PATENT DOCUMENTS

| | | | | |
|---|---|---|---|---|
| 4,710,864 A | * | 12/1987 | Li | 700/47 |
| 4,924,408 A | * | 5/1990 | Highland | 706/60 |
| 4,937,755 A | * | 6/1990 | Yokota et al. | 716/3 |
| 4,981,961 A | * | 1/1991 | Ngo | 530/364 |
| 5,119,318 A | * | 6/1992 | Paradies et al. | 706/52 |
| 5,136,523 A | * | 8/1992 | Landers | 706/50 |
| 5,208,765 A | * | 5/1993 | Turnbull | 702/84 |
| 5,253,331 A | * | 10/1993 | Lorenzen et al. | 706/45 |
| 5,434,971 A | | 7/1995 | Lysakowski, Jr. | 395/200 |
| 5,446,575 A | | 8/1995 | Lysakowski, Jr. | 395/200.01 |
| 5,546,301 A | * | 8/1996 | Agrawal et al. | 700/23 |
| 5,569,799 A | * | 10/1996 | Chen et al. | 570/261 |
| 5,576,946 A | | 11/1996 | Bender et al. | 364/146 |
| 5,581,659 A | * | 12/1996 | Takatori | 706/19 |
| 5,623,592 A | | 4/1997 | Carlson et al. | 395/348 |

(Continued)

FOREIGN PATENT DOCUMENTS

EP      0 796 654 A2      9/1997

(Continued)

OTHER PUBLICATIONS

Lennon et al; Using a distributed mini-computer network to automate a biochemical laboratory; Proceedings of the ACM SIGMINI/SIGPLAN interface meeting on Programming systems in the small processor environment; Mar. 1976; vol. 11, Iss. 4.*

(Continued)

*Primary Examiner*—Anthony Knight
*Assistant Examiner*—Nathan H. Brown, Jr.

(57) ABSTRACT

Methods, apparatus, and business processes enabling individual chemists to design, order, and obtain data for multiple experiments or measurements in a timely and cost-effective manner. In particular implementations, the invention includes methods and apparatus for designing sets of custom experiments, ordering the execution of the experiments, communicating the order to a remote laboratory, executing the experiments at that laboratory using high-throughput technologies, and communicating the experimental results to the user.

76 Claims, 4 Drawing Sheets

U.S. PATENT DOCUMENTS

| | | | | |
|---|---|---|---|---|
| 5,631,844 | A | | 5/1997 | Margrey et al. .............. 702/22 |
| 5,703,792 | A | * | 12/1997 | Chapman ..................... 702/27 |
| 5,726,914 | A | | 3/1998 | Janovski et al. .............. 702/84 |
| 5,727,127 | A | * | 3/1998 | Schulze Horn et al. ....... 706/52 |
| 5,737,494 | A | * | 4/1998 | Guinta et al. ................ 706/47 |
| 5,737,498 | A | | 4/1998 | Murray ........................ 395/81 |
| 5,754,737 | A | * | 5/1998 | Gipson ........................ 706/11 |
| 5,761,381 | A | * | 6/1998 | Arci et al. .................... 706/13 |
| 5,778,154 | A | * | 7/1998 | Bone et al. ................... 706/47 |
| 5,808,918 | A | * | 9/1998 | Fink et al. .................... 703/11 |
| 5,812,405 | A | * | 9/1998 | Meredith, Jr. ................ 700/157 |
| 5,815,638 | A | * | 9/1998 | Lenz et al. .................... 706/15 |
| 5,841,975 | A | | 11/1998 | Layne et al. ................. 709/203 |
| 5,849,578 | A | * | 12/1998 | Falb ............................ 435/325 |
| 5,959,297 | A | * | 9/1999 | Weinberg et al. ........... 250/288 |
| 5,961,923 | A | * | 10/1999 | Nova et al. .................. 422/68.1 |
| 5,969,121 | A | * | 10/1999 | Allen et al. .................. 536/23.1 |
| 5,985,356 | A | * | 11/1999 | Schultz et al. ................ 427/8 |
| 6,004,617 | A | * | 12/1999 | Schultz et al. ................ 427/8 |
| 6,017,496 | A | * | 1/2000 | Nova et al. .................. 422/68.1 |
| 6,029,157 | A | * | 2/2000 | Mihatsch ...................... 706/15 |
| 6,030,917 | A | * | 2/2000 | Weinberg et al. ........... 502/104 |
| 6,031,625 | A | | 2/2000 | Sherman et al. ........... 358/1.18 |
| 6,034,212 | A | * | 3/2000 | Sudol et al. ................. 530/324 |
| 6,034,775 | A | * | 3/2000 | McFarland et al. ......... 356/364 |
| 6,044,212 | A | | 3/2000 | Flavin et al. ................. 703/6 |
| 6,045,671 | A | * | 4/2000 | Wu et al. ............... 204/298.11 |
| 6,085,227 | A | | 7/2000 | Edlund et al. .............. 709/203 |
| 6,087,181 | A | * | 7/2000 | Cong .......................... 436/37 |
| 6,125,383 | A | | 9/2000 | Glynias et al. ............. 709/202 |
| 6,149,882 | A | * | 11/2000 | Guan et al. .................. 422/211 |
| 6,151,123 | A | * | 11/2000 | Nielsen ....................... 356/445 |
| 6,157,449 | A | * | 12/2000 | Hajduk ....................... 356/367 |
| 6,175,409 | B1 | * | 1/2001 | Nielsen et al. .............. 356/337 |
| 6,175,816 | B1 | | 1/2001 | Flavin et al. ................ 703/13 |
| 6,192,320 | B1 | | 2/2001 | Margrey et al. .............. 702/84 |
| 6,260,407 | B1 | * | 7/2001 | Petro et al. ................. 73/61.52 |
| 6,265,226 | B1 | * | 7/2001 | Petro et al. .................. 436/180 |
| 6,284,459 | B1 | * | 9/2001 | Nova et al. ................... 435/6 |
| 6,294,388 | B1 | * | 9/2001 | Petro ........................... 436/8 |
| 6,296,771 | B1 | * | 10/2001 | Miroslav ................... 210/656 |
| 6,306,658 | B1 | * | 10/2001 | Turner et al. ............... 436/37 |
| 6,329,139 | B1 | * | 12/2001 | Nova et al. ................... 435/6 |
| 6,340,595 | B1 | * | 1/2002 | Vogels et al. .............. 435/457 |
| 6,364,956 | B1 | * | 4/2002 | Wang et al. ................ 118/726 |
| 6,373,570 | B1 | * | 4/2002 | McFarland et al. ......... 356/364 |
| 6,395,552 | B1 | * | 5/2002 | Borade et al. ............... 436/37 |
| 6,410,332 | B1 | * | 6/2002 | Desrosiers et al. ........... 436/37 |
| 6,411,945 | B1 | | 6/2002 | Nakajima .................... 706/19 |
| 6,421,612 | B1 | * | 7/2002 | Agrafiotis et al. ............ 702/19 |
| 6,453,333 | B1 | | 9/2002 | Glynias et al. ............. 709/202 |
| 6,485,692 | B1 | * | 11/2002 | Freitag et al. .............. 422/130 |
| 6,507,945 | B1 | * | 1/2003 | Rust et al. .................. 717/103 |
| 6,528,026 | B2 | * | 3/2003 | Hajduk et al. .............. 422/198 |
| 6,535,824 | B1 | * | 3/2003 | Mansky et al. .............. 702/30 |
| 6,536,944 | B1 | * | 3/2003 | Archibald et al. ............. 374/20 |
| 6,541,271 | B1 | * | 4/2003 | McFarland et al. ......... 436/171 |
| 6,548,026 | B1 | * | 4/2003 | Dales et al. ................ 422/138 |
| 6,581,020 | B1 | | 6/2003 | Buote et al. ................ 702/123 |
| 6,584,412 | B1 | | 6/2003 | Brecher ....................... 702/27 |
| 6,594,588 | B1 | | 7/2003 | Peden et al. ................. 702/32 |
| 6,618,852 | B1 | | 9/2003 | Van Eikeren et al. ....... 717/108 |
| 6,640,191 | B1 | | 10/2003 | Deem et al. ................. 702/19 |
| 6,647,358 | B2 | * | 11/2003 | Grass et al. .................. 703/2 |
| 6,658,429 | B2 | * | 12/2003 | Dorsett, Jr. ................... 707/1 |
| 6,681,198 | B2 | | 1/2004 | Buote et al. ................ 702/185 |
| 6,720,186 | B1 | * | 4/2004 | Turner et al. ................ 436/37 |
| 6,749,814 | B1 | * | 6/2004 | Bergh et al. ................ 422/130 |
| 6,864,201 | B2 | * | 3/2005 | Schultz et al. .............. 502/64 |
| 6,901,393 | B1 | * | 5/2005 | Owen et al. ................. 706/46 |
| 2001/0047398 | A1 | | 11/2001 | Rubenstein ................ 709/218 |
| 2001/0053528 | A1 | * | 12/2001 | Boussie et al. .............. 435/7.1 |
| 2003/0043429 | A1 | * | 3/2003 | Dumble et al. ............. 359/124 |
| 2005/0060305 | A1 | * | 3/2005 | Hopkins et al. .............. 707/3 |

FOREIGN PATENT DOCUMENTS

| | | |
|---|---|---|
| WO | WO 91/06050 | 5/1991 |
| WO | WO 9732208 A1 * | 9/1997 |
| WO | WO 98/15825 | 4/1998 |
| WO | WO 00/23921 | 4/2000 |
| WO | WO 01/65415 | 9/2001 |

OTHER PUBLICATIONS

Lee et al; Statistical experimental design for MBE process characterization; Nineteenth IEEE/CPMT Electronics Manufacturing Technology Symposium; Oct.14-16, 1996; pp. 378-385.*

May et al; Recipe synthesis for PECVD SiO2 films using neural networks and genetic algorithms; 46th Proceedings Electronic Components and Technology Conference; May 28-31, 1996; pp. 855-860.*

Vanrolleghem; The adaptive sensor concept: on-line modelling of the activated sludge process with optimal in-sensor-experiments; Proceedings of the Third IEEE Conference on Control Applications; Aug. 24-26, 1994; pp. 1017-1022; vol. 2.*

Brecher J.S., *Chimia* 1998 52 658-663.

Chemscape Affystore, Application News, Molecular Connection, Jan. 1998, pp. 14-17.

Chemscape Enhancements, Product News, Molecular Connection, Jan. 1998, pp. 12-13, 24.

Chemscape, Molecular Connection, Apr. 1998, pp. 13, 15-16.

Culot, L., WebServer @ RiboTargets, ChemOffice WebServer Reviews, CambridgeSoft Corporation 1999, 3 pages, pp. 1-3.

Fowler et al., "Experience with the Virtual Notebook System: Abstraction in Hypertext", Association of Computing Machinery 1994 pp. 133-143.

Gelin, Bruce R. Ph.D., ChemOffice WebServer: the Newest Web Technology, ChemOffice WebServer Reviews, CambridgeSoft Corporation 1999, 4 pages, pp. 1-4.

Gelin, Bruce R. Ph.D., Managing Chemical Inventory with CIS Pro, ChemOffice WebServer Reviews, CambridgeSoft Corporation 1999, 5 pages, pp. 1-5.

Gosalvez, David Ph.D., Chemical Catalogs go E-Commerce, ChemOffice WebServer Reviews, CambridgeSoft Corporation 1999, 3 pages, pp. 1-3.

Keating et al., "Development and Use of a Virtual NMR Facility", J. of Magnetic Resonance 143 2000 pp. 172-183.

Kouzes et al., "Collaboratories: Doing Science on the Internet", IEEE Computer, vol. 29, 8, Aug. 1996, http://collaboratory.emsl.pnl.gov/presentations/papers/IEEECollaboratories.html.

Manrique, J., Electronic Notebooks for Chemical R&D, ChemOffice WebServer Reviews, CambridgeSoft Corporation 1999, 2 pages, pp. 1-4.

Mendoza Electronic Laboratory Notebook, Environmental Molecular Sciences Laboratory, Computing & Information Sciences, Pacific Northwest National Laboratory, http://collaboratory.emsl.pnl.gov/presentations/papers/ACMpaper.html, May 19, 1998, 24 slides, pp. 1-24.

Meyers "eResearch: The Rise of Scientific Virtual Facilities", Proceedings of the 1999 International Chemical Information Conference, ISBN: 1-873699-63-8, 196 pages, by Infonortics Ltd., http://collaboratory.emsl.pnl.gov/presentations/papers/eresearch.france.html Oct. 28-30, 1999, pp. 1-7.

Myers et al., "Electronic Laboratory Notebooks for Collaborative Research", Proceedings of the IEEE Fifth Workshops on Enabling Technology: Infrastructure for Collaborative Enterprises (WET ICE '96), Jun. 19-21, 1996, Stanford, California, http://collaboratory.emsl.pnl.gov/presentations/papers/notebook.wetice96.html, pp. 1-10.

Payne et al. "The EMSL Collaborative Research Environment (CORE)—Collaboration via the World Wide Web", http://collaboratory.emsl.pnl.gov/presentations/papers/core.wetice96.html Jun. 19-21, 1996, pp. 1-10.

MDL Screen™ User's Guide, "MDL's Solution for High-Throughput Screening Data Management", © Copyright 1996 by MDL Information Systems, Inc., pp. 1-2 to 14-6.

U.S. Appl. No. 09/174,856, filed Oct. 19, 1998, Lacy et al.

U.S. Appl. No. 09/420,334, filed Oct. 18, 1999, Lacy et al.

Aikens, J. and Kirchoff, E., "Automated Process Research, A New Tool for Eliminating R&D Bottlenecks," *Chemical Bond*, SOCMA, Oct.-Nov. 1999, 2 pages (page numbers unknown).

Incyte Genomics, In., *"Umpire Data Analysis System"*, Feb. 17, 2000, <http//www.incyte.com/sequencing/images/umpire-screen.jpg>.

Chemical Concepts, *"SpecInfo XS"*, Mar. 17, 2000, <http://www.chemicalconcepts.com/p1123.htm>.

Chemical Concepts, *"Spectacle XS"*, Mar. 17, 2000, <http://www.chemicalconcepts.com/p1124.htm>.

Chemical Concepts, *"SpecSurf XS"*, Mar. 17, 2000, <http://www.chemicalconcepts.com/p1125:htm>.

Chemical Concepts, *"SpecInfo on the Internet"*, Mar. 17, 2000, <http://www.chemicalconcepts.com/p111.htm>.

Incyte Genomics, Inc., *"Incyte Contract Sequencing"*, Feb. 17, 2000, <http://www.incyte.com/sequencing/index.html>.

Incyte Genomics, Inc., *"State-of-the-Art Sequencing"*, Feb. 17, 2000, <http://www.incyte.com/sequencing/operation.html>.

Incyte Genomics, Inc., *"Umpire Data Analysis System"*, Feb. 17, 2000, <http://www.incyte.com/sequencing/umpire.html>.

Incyte Genomics, Inc., *"Automated Sample Preparation Robot"*, Feb. 17, 2000, <http://www.incyte.com/sequencing/robot.html>.

Incyte Genomics, Inc., *"Request a Free Estimate", Contract Sequencing*, Feb. 17, 2000, <http://www.incyte.com/sequencing/estimate.html>.

Lab Control Scientific Consulting and Software Development GmbH, *"Comprehensive Spectroscopy Workstation,"* Mar. 17, 2000, <http://www.labcontrol.com/pro/work/specwin/winspec/index.html>.

Ann M. Thayer, *"Bioinformatics for the Masses"*, Mar. 22, 2000, <http://pubs.acs.org/hotartcl/cenear/00207/7806bus1.html>.

Chemical Concepts, *"Products—Frameset"*, Mar. 17, 2000, <http://www.chemicalconcepts.com/products.htm>.

Chemical Concepts, *"Inhouse"*, Mar. 17, 2000, <http://www.chemicalconcepts.com/p112.htm>.

Chemical Concepts, *"Inhouse—The Server"*, Mar. 17, 2000, <http://www.chemicalconcepts.com/p1121.htm>.

Chemical Concepts, *"Available SpecInfo databases"*, Mar. 17, 2000, <http://www.chemicalconcepts.com/p1122.htm>.

Kagaku, "Combinatorial Chemistry: Inconceivable without Computer", *Combinatorial Chemistry*, vol. 51, No. 8, pp. 480-483 & 583 (1996). Original Japanese reference and English translation included.

Yamagata et al., "Constructing an Assay System with HTS", *IV High Throughout Screening*, pp. 179-191 (1997). Original Japanese reference and English translation included.

Vogel Scientific Sof, Nov. 6, 2002, 1996, Volume, 27 pages, Website, Ciara Chemical Information And Reaction Assistant, Ciara Product Description www.vogelscientific.com/ciara.htm.

Butcher, 1998, vol. 17, pp. 16-17, Molecular Connection, Synaptic Smoothes Data Flow Between Chemistry And Biology, Jul.

Kovacevich, 1998, vol. 17, pp. 14-15, Molecular Connection, Integrated Data Management Lets Monsanto Reap The Benefits Of Automation, Jul.

Weintraub, 1998, vol. 17, pp. 12-13,18, Molecular Connection, Helios Manages The Data Flow from Library To Synthesizer, Jul.

Seega, 1998, vol. 17, 5 pages incl. 4-5,24, Molecular Connection, BASF Partners With MDL To Build Corporate-Wide Discovery Solution, Jan.

MDL, 1998, vol. 17, 4 pages, (incl 22-23), Molecular Connection, MDL Screen 1.3 Closes Final Gap In HTS Workflow, Jan.

MDL, 1998, vol. 17, pp. 12,14,16, Molecular Connection, Bayer Integrates Legacy Reaction Data With Reaction Browser 2.0, Apr.

Puckett, W., 1998, vol. 17, pp. 10-11, Molecular Connection, MDL/Surety Partnership Helps Buckman "Insure" R&D Data, Apr.

MDL, 2000, Volume, pp. 6-13, Molecular Connection, Working With Focused Libraries Using MDL Software And Argonaut Instrumentation Winter.

MDL, 2000, Volume, p. 5, Molecular Connection, MDL Acquires Afferent And Launches Afferent TeamWorks 3.0 To Support Discovery Chemistry Project Teams, Winter.

MDL, 1998, vol. 17, pp. 20-21, Molecular Connection, The Life Science Workbench Getting Biologists Back To The Bench, Oct.

Ellman, 1998, vol. 17, pp. 11-18, Molecular Connection, MDL Announces New Tools Supporting High-Throughput Chemistry, Oct.

Haag, 1998, vol. 17, pp. 6-11, Molecular Connection, Automating The Discovery Process, Jul.

McKenna, Drew, 1998, vol. 17, pp. 6-9, Molecular Connection, Inventory Management: The Key To Industrializing Discovery, Apr.

MDL, 2000, Volume, p. 5, Molecular Connection, MDL And Chemdex Agree To Integrate E-Commerce And Discovery Informatics Solutions, Spring.

Watthney, 1998, vol. 17, pp. 8-10, Molecular Connection, MDL Software Supports, Oct.

MDL, 1998, vol. 17, pp. 19, Molecular Connection, Working With Cheminformatics Business Rules, Oct.

Chemexper, 1999, Volume, 117 pages, User Manual, Expereact Userguide www.chemexper.com.

Sachs and Myers, "WETICE'96: Workshop on Electronic Notebooks", Working Group Report 1996, pp. 1-12.

Sachs et al., "Design of the DOE2000 Electronic Notebook[1]: LBNL Components", Dec. 1997 16 pages, pp. 1-16.

Sachs et al., "Electronic Notebooks for Distributed Collaboratories: envisioned research and development," http://web.archive.org/web/19970606001930/http://www-itg.lbl.gov/~ssachs/notebook/no..., Nov. 1995, pp. 1-5.

Sachs et al., "The Spectro-Microscopy Electronic Notebook[1]", Technical Report LBNL-39886, Jan. 1997, 17 pages, pp. 1-17.

Schur et al., "Collaborative Suites For Experiment-Oriented Scientific Research", Interactions, 1998, pp. 1-12.

Shipman et al., "Distributed Hypertext for Collaborative Research: The Virtual Notebook System", Hypertext '89 Proceedings, Association of Computing Machinery, Nov. 1989, pp. 129-135.

Swartz, M., Building Web Applications, ChemOffice WebServer Reviews, CambridgeSoft Corporation 1999, 2 pages, pp. 1-2.

Swartz, M., ChemOffice Integrates Oracle and Web Browsers, ChemOffice WebServer Reviews, CambridgeSoft Corporation 1999, 5 pages, pp. 1-5.

Swartz, M., Combinatorial Chemistry with ChemOffice, ChemOffice WebServer Reviews, CambridgeSoft Corporation 1999, 6 pages, pp. 1-6.

Swartz, M., Register Molecules with WebServer, ChemOffice WebServer Reviews, CambridgeSoft Corporation 1999, 4 pages, pp. 1-4.

* cited by examiner

REMOTE EXECUTION OF MATERIALS LIBRARY DESIGNS

CROSS-REFERENCE TO RELATED APPLICATIONS

This application claims the benefit of U.S. Provisional Application No. 60/191,783, filed on Mar. 24, 2000, which is incorporated by reference herein.

BACKGROUND

This invention relates to a system and methods for conducting experimental research. Research and development is often the most expensive and unpredictable activity in a corporation. Well-equipped laboratories, highly skilled scientists, and high-risk programs are necessary components of R&D efforts. Unlike manufacturing, supply chains, marketing, or sales activities, it is difficult to control the output or efficiency of R&D. Inventions cannot be predicted and scheduled, and, thus, timelines in R&D are measured in years. In addition, research is typically undertaken by one-at-a-time experimental approaches, and, thus, the resulting costs per experiment associated with R&D are enormous.

For example, at the time this application is being filed, the average, fully burdened cost of a staff scientist and a research assistant in the United States is estimated to be $500,000. This pair of researchers would be extremely productive if they executed 1000 experiments per year. Therefore, the cost per experiment for this pair of researchers is at least $500.

As product development cycles continue to shrink in every industry, competition increases, and pressure to grow and build businesses mounts, R&D organizations must increase their innovation rate and productivity significantly. During the past decade, technologies have emerged in pharmaceutical research, chemicals research, and materials science research to improve the effectiveness of R&D. These technologies are based on high-throughput technologies that enable the execution of 100 to 10,000 times more experiments per unit time compared to traditional research approaches. High-throughput technologies merge automation, miniaturization, informatics, chemistry, and physics to create systems that rapidly synthesize, process, screen, and analyze compounds, mixtures, or compositions of matter. With these technologies, the cost per experiment can drop to tens of dollars and time scales can be reduced from years to weeks or months.

In general, access to high-throughput technologies is limited to large conglomerates that can afford to create specific technologies internally or to pay specialized companies for exclusive access. Even within large conglomerates, only a fraction of the R&D organization has access to these state-of-the-art research platforms. The main limitation to broad access is the overall expense in building a capability that enables the execution of at least 100,000 experiments per year. It is necessary to spend millions of dollars to build the capability and it is not possible to spend $\frac{1}{10}$ or $\frac{1}{100}$ the amount to get $\frac{1}{10}$ or $\frac{1}{100}$ of the experimental throughput.

Individual chemists within large and small organizations often cannot effectively access high-throughput technologies, yet these technologies are essential to compete and to increase R&D efficiency and the rate of innovation. Accordingly, there is a need for methodologies, apparatus, and/or business processes which enable chemists to design, order, and obtain data to a plurality of experiments or measurements in a timely and cost-effective manner.

SUMMARY

In general, in one aspect, the invention provides methods and apparatus, including computer program apparatus, implementing techniques for carrying out a set of experiments. The techniques can include providing a remote user at a first location with an experiment design tool for generating an experiment design defining a set of experiments; receiving at a second location a user input including an experiment design; preparing a multi-member library of materials corresponding to an experiment matrix defined in the experiment design; applying one or more process conditions to the members of the library of materials to transform at least one starting material into a product; applying a screening method defined by the first experiment design to generate experimental results; and providing the experimental results to the remote user. The experiment design includes an experiment matrix having a plurality of matrix elements, one or more starting materials assigned to the matrix elements and one or more process conditions to be applied to the matrix elements. Each of a plurality of matrix elements is defined by a unique combination of starting materials and/or process conditions. The experiment design also defines a screening method to be applied to generate the experimental results. The second location is remote from the first location.

Particular advantageous implementations can include one or more of the following features. The screening method can be a high throughput screening method. The screening method can be selected from infrared thermography, chromatography, capillary electrophoresis, mass spectrometry, optical reflection, optical transmission, viscometry, mechanical resonators, solubility, differential scanning calorimetry, elongation, indentation, deformation or spectroscopy. The experiment matrix can include at least 50, or more preferably at least 96 elements, and the experimental results can be provided to the user within 20 days, or more preferably within 10 days from preparation of the library. The experiment matrix can include at least 1000 elements, and the experimental results can be provided to the user within 50 days, more preferably 20 day, still more preferably 10 days, from preparation of the library. The techniques can include in response to providing the experimental results, receiving another user input including a second experiment design defining additional experiments; preparing a second library of materials based on the second experiment design; applying one or more process conditions to the second library of materials to transform at least one of the starting materials into a product and applying a second screening method to generate additional experimental results; and providing the additional experimental results to the remote user. The second library of materials can be a superset of the first library of materials. The second screening method and the first screening method can be different. The experiment design tool can include a user interface configured to enable the remote user to select materials from a list of materials in a remote material inventory, to select processing conditions from a list of processing conditions that can be implemented by a remote process control system, or to select high throughput screening methods from a list of screening methods that can be performed by one or more screening instruments available at a remote laboratory location. The experiment design tool can include a user interface configured to access one or more databases of available materials, process conditions and high throughput screening methods. The first screening method can be automatically defined based on one or more of the starting materials and process conditions. The techniques can include evaluating the experiment design before preparing the library of materials to generate an experimental plan describing a proposed execution of the set of experiments, and providing the experimental plan to the remote user. Evaluating the experiment design can include generating an estimate of time and/or cost to perform the set of experiments defined by the experiment design. Evaluating the experiment design can include determining whether the design conforms to a set of experiment parameters, and, if not, communicating to the remote user that one or more experiments defined by the experiment design cannot be executed. Determining whether the design conforms to the set of experiment parameters can include determining whether the assigned starting materials specified in the first experiment design are present in an inventory of materials. Evaluating the experiment design can include determining whether the assigned starting materials have chemical or physical properties falling within a predetermined set of chemical or physical properties. The experiment design tool can be configured to enable the remote user to generate an experiment request for execution of the set of experiments defined by the first experiment design for submission over a computer network. The experiment design can be received from the remote user over a computer network. The first experiment design can include information identifying one or more custom materials assigned to one or more matrix elements. The techniques can include receiving custom materials from the remote user for use in preparing the library of materials. The first experiment design can define a set of experiments directed to chemicatalysis or biocatalysis, optimization of a chemical synthetic process or polymerization. The set of experiments can be directed to the preparation of pharmaceutical products or intermediates, fine chemicals, specialty chemicals, commodity chemicals, polymeric coatings, adhesives, dispersants, surfactants, additives, electronic materials, composites or alloys. The user can receive the experimental results by accessing a results database through a remote computer-implemented interactive user interface. The techniques can include, in response to providing the experimental results, receiving a second user input including a request to purchase a starting material or product corresponding to one of the elements of the experiment matrix. The experiment design tool can be provided as a computer program to be executed by a computer system at the first location, or as a computer program executed by a server process running at the second location, in which case the remote user can access the experiment design tool using a client process running at the first location.

In general, in another aspect, the invention provides methods and apparatus, including computer program apparatus, implementing techniques for obtaining experimental results for a set of experiments. The techniques can include generating an experiment design defining a set of experiments; communicating the experiment design to a remote laboratory for execution; receiving an experimental plan describing a proposed execution of the set of experiments; communicating an approval of the experimental plan to the remote laboratory if the proposed execution of the set of experiments is acceptable; and receiving experimental results obtained at the remote laboratory by applying one or more specified process conditions to a library of materials corresponding to an experiment matrix defined in the experiment design to transform at least one of the starting materials into a product and applying a specified screening method. The experiment design includes an experiment matrix having a plurality of elements, one or more starting materials assigned to the matrix elements, and one or more process conditions to be applied to the matrix elements. Each of a plurality of the matrix elements is defined by a unique combination of starting materials and process conditions. The experiment design also defines a screening method to be applied to generate the experimental results. The experimental plan can include an estimate of time and/or cost to perform the set of experiments.

In general, in another aspect, the invention provides methods and apparatus, including computer program apparatus, implementing techniques for designing a set of experiments for execution by a remote laboratory. The techniques can include defining an experiment matrix having a plurality of matrix elements corresponding to locations in a library of materials; designating one or more starting materials and assigning each starting material to one or more matrix elements, and designating at least one processing condition to be applied to one or more elements of the experiment matrix; designating a screening method to be applied to one or more elements of the experiment matrix; and communicating an experiment design to the remote laboratory. Each of a plurality of matrix elements is defined by a unique combination of starting materials and/or process conditions. The experiment design includes the experiment matrix and the screening method designation.

Particular advantageous implementations can include one or more of the following features. The starting materials can be selected from a list of materials in a remote material inventory. The processing conditions can be selected from a list of processing conditions that can be implemented by a remote process control system. The screening method can be selected from a list of screening methods that can be performed by one or more remote screening instruments. The screening method can be automatically defined based on one or more of the starting materials and process conditions. The experiment design can be communicated to the remote laboratory over a computer network.

In general, in another aspect, the invention provides a computer-implemented research system for carrying out a set of experiments. The system includes a computer-implemented remote experiment design tool for generating an experiment design defining a set of experiments, a user interface subsystem configured to receive an experiment design generated by the experiment design tool and to provide experimental results to a user, and a research engine configured to evaluate the experiment design, generate an experimental plan describing a proposed execution of the set of experiments, and prepare a library of materials corresponding to the experiment matrix according to the experimental plan. The experiment design includes an experiment matrix having a plurality of matrix elements, one or more starting materials assigned to the matrix elements and one or more process conditions to be applied to the matrix elements. Each of a plurality of matrix elements is defined by a unique combination of starting materials and process conditions. The experiment design also defines a screening method to be applied to generate experimental results. The library of materials has a plurality of members, each of which contains the starting materials assigned to a corresponding matrix element. The research engine is operable to apply the process conditions to the members of the library of materials to transform at least one of the starting materials into a product and to apply the screening method to generate experimental results.

Particular advantageous implementations can include one or more of the following features. The system can include an inventory subsystem including an inventory database storing information identifying a plurality of materials in a material inventory. The system can include one or more automated instruments coupled to the research engine. The research engine can include a process database storing information identifying a plurality of chemical processes capable of being performed by the one or more automated instruments. The research engine can include an experiment database storing information about one or more sets of experiments executed on behalf of the remote user.

The details of one or more embodiments of the invention are set forth in the accompanying drawings and the description below. Other features, objects, and advantages of the invention will be apparent from the description and drawings, and from the claims.

DESCRIPTION OF DRAWINGS

Like reference symbols in the various drawings indicate like elements.

DETAILED DESCRIPTION

The invention relates to a research system to connect remote scientists ("users") with laboratory facilities for performing experimental research. The research system permits users to design one or more sets of experiments, to submit an order for the experiments to be carried out at remote laboratory facilities, and to obtain experimental results. In general, users can include individuals, academic scientists and those employed in industry, including, for example, fine chemicals, specialty chemicals, commodity chemicals, petrochemicals, specialty polymers, biotechnology and biosciences, pharmaceuticals, formulations, and the like. The research system can be configured to execute experiments relating to, for example, chemicals or materials synthesis, catalytic reactions, polymerization reactions, formulations, analysis of chemicals or materials, or measuring chemical or material properties. Appropriate experiments can include (which, in this specification, is used in its open-ended sense, to mean that other elements or steps are not excluded) those in the fields of fine, specialty or commodity chemicals (such as chemi- or biocatalysis (either heterogeneous or homogeneous) or process development), specialty polymers (such as coatings, adhesives, dispersants, surfactants or additives), electronic materials and structural materials (such as composites or alloys).

Figure 1:
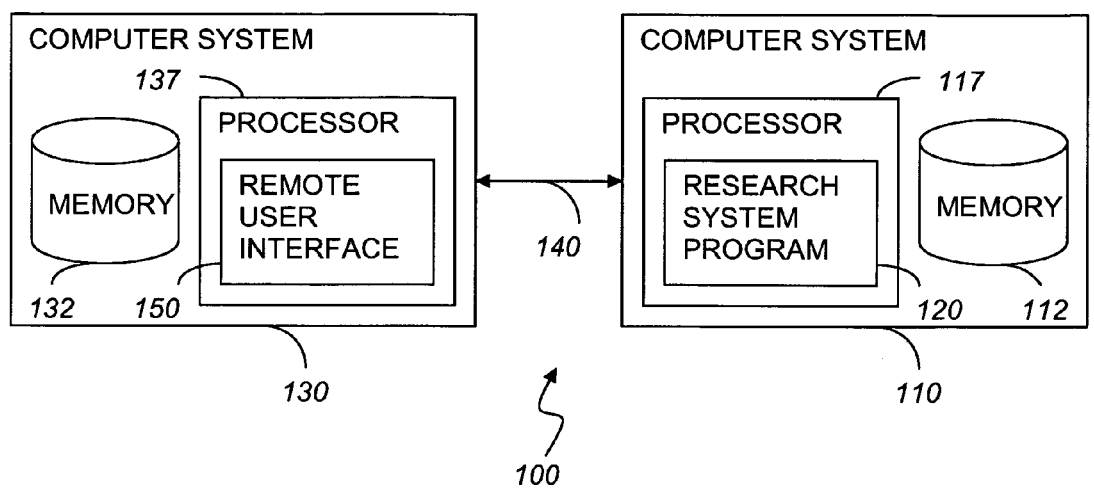
FIG. 1 is a schematic diagram of a computer network connected to a research system that can be used to practice the present invention.

FIG. 1 illustrates a research system 100 that includes a general-purpose programmable digital computer system 110 of conventional construction, including a memory 112 and a processor 117 for running a research system program 120. Computer system 110 also includes conventional communications hardware and software by which computer system 110 can be connected to other computer systems, including a user's computer system 130 including a memory 132 and a processor 137 running a remote user interface program 150, by a computer network 140, such as a local area network, wide area network or the internet. Although FIG. 1 illustrates each computer system as a single computer, the functions of each system can be distributed on a network.

Figure 2:
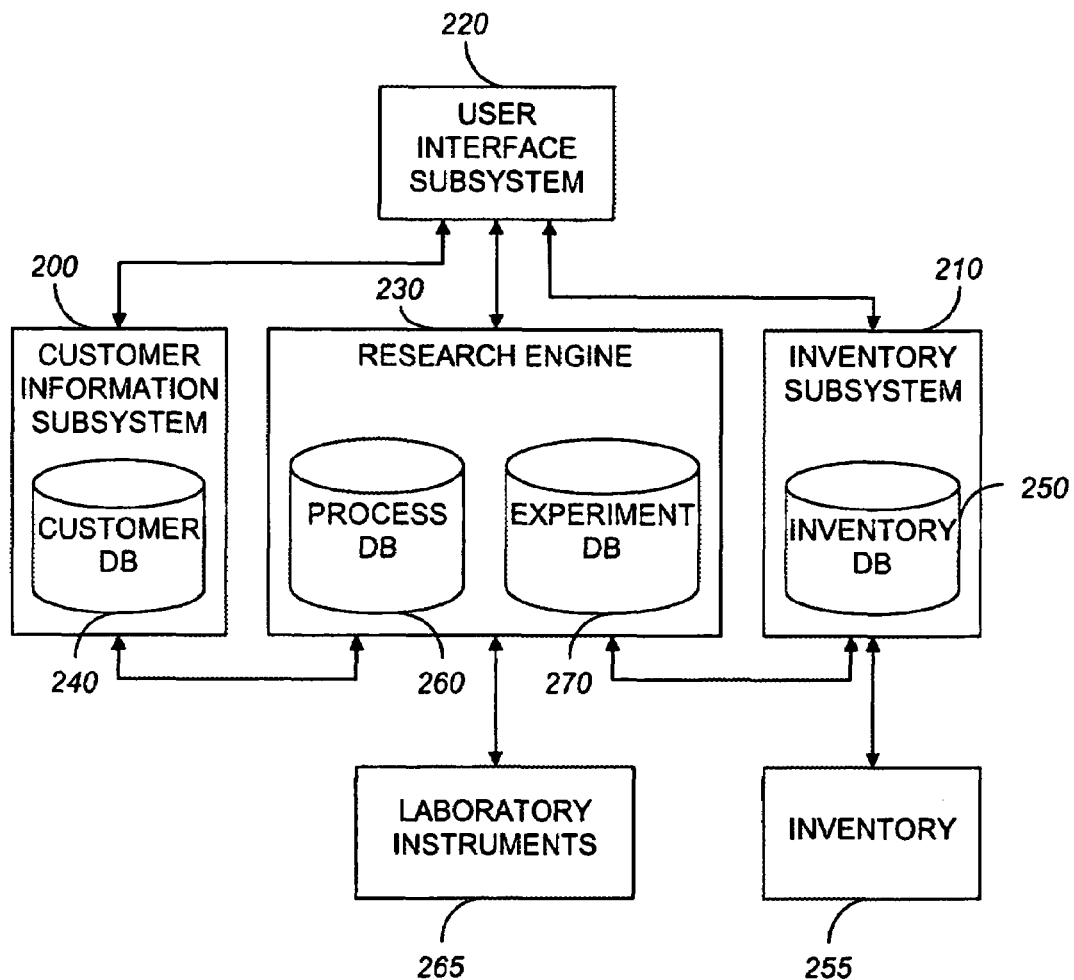
FIG. 2 is a schematic diagram illustrating a research system that can be used to practice the present invention.

As shown in FIG. 2, research system 100 includes a customer information subsystem 200, an inventory subsystem 210, a user interface subsystem 220, and a research engine 230. Customer information subsystem 200 uses a customer database 240 to track and update information about users. Customer database 240 includes information about each user, such as the user's name, contact information, identification code and password. Customer database 240 can also include information such as a user's organizational affiliation, information about the business of the user or the user's organization, a history of previous experiment requests by the user or others affiliated with the user's organization or specialized information about materials and experimental methods provided by the user for use by research system 100. In a preferred implementation, computer systems 110 and 130 are located at separate locations remote from each other, and the user is a remote user whose relationship with the operator of research system 100 is that of a customer to with a merchant or service provider, and has no other affiliation with the operator of research system 100.

Inventory subsystem 210 uses an inventory database 250 to track and update information about materials in an inventory 255 that are available for use in experiments to be performed by research system 100. The inventory database 250 includes inventory information about each material in inventory 255, which can include, for example, chemical reagents, substrates, catalysts, stabilizers, additives, solvents, monomers, resins, polymers, supports, zeolites, molecular sieves, ligands, metal precursors, metal salts, metal oxides, metal complexes and the like, and which can include materials that are in the public domain as well as proprietary materials. For each material in inventory 255, this information includes a material name or description, an inventory amount reflecting the quantity of the material currently available for use by research system 100 and a customer price. Inventory database 250 can also include other information, such as an image or chemical structure for the material, a description of material properties or characteristics, a material category classifying the material according to chemical process, functionality or reactivity (such as, for example, reagent, catalyst, substrate, monomer, initiator, accelerator, quenching agent or like categories), a recipe for preparation of the material (either manually or by automated means) and internal accounting information such as a supplier of the material, a cost to order, a quantity currently on order and the like. Optionally, inventory database 250 can also include specialized information about materials provided by users for use by research system 100.

User interface subsystem 220 uses information from customer database 240, inventory database 250 and process database 260 to enable users to design experiments to be performed by research system 100 and to submit those experiment designs to research system 100 in the form of experiment requests. Process database 260 includes information about the types of processes that can be performed by research system 100, such as, for example, particular chemistries (that is, types of transformations to be carried out on specified starting materials) or analytical techniques that can be carried out using instruments 265 coupled to research system 100. Particular chemistries can include, for example, homogeneous or heterogeneous catalysis reactions (including single phase, multiple phase and phase transfer catalysis including ionic liquids) using a variety of reactors, directed to reactions that include activation of and/or formation of H—Si; H—H; H—N; H—O; H—P; H—S; C—H; C—C; C=C; C C; C-halogen; C—N; C=N; C N; C—O; C=O; C—S; C—P and C—Si bonds. Classes of reactions that can be performed by research system 100 include aliphatic nucleophilic or electrophilic substitution; aromatic nucleophilic or electrophilic substitution; free radical substitution, addition reactions to carbon—carbon or carbon-hetero multiple bonds; elimination reactions; rearrangement reactions; oxidations and reductions; and biocatalysis performing reactions such as oxido-reductases, transferases, hydrolases, lyases, isomerases and ligases. Specifically, such reactions include oxidation; carbonylation; hydroxylation; hydroformylation; hydroxycarbonylation; hydrocarbonylation; hydroesterification; hydrogenation; transfer hydrogenation; hydrosilylation; hydroboration; hydroamination; epoxidation; aziridation; halogenation; hydrolysis; reductive amination; C—H activation; insertion; C—H activation-insertion; C—H activation-substitution; C-halogen activation; C-halogen activation-substitution; C-halogen activation-insertion; cyclopropanation; cross-coupling reactions; Friedel-Crafts reactions; alkene metathesis; alkene oligomerization; alkene polymerization; alkyne oligomerization; alkyne polymerization; co-polymerization; CO-alkene co-oligomerization; CO-alkene co-polymerization; CO-alkyne co-oligomerization and CO-alkyne co-polymerization. In addition to organic chemical transformations involving the formation or cleavage of covalent chemical bonds, appropriate chemistries can include the formation of mixtures, composites or alloys synthesis of organic, inorganic and organometallic compounds, liquid or solid state synthesis and other material transformations.

Process conditions suitable for optimization or variation using research system 100 can include, for example, temperature, pressure, concentration (moles, mass or volume), rate and order of addition, solvent or mixing rate. Research system 100 can be used to optimize specific process steps, such as distillation (at various pressures), liquid—liquid extraction, crystallization (e.g., crystallite size or morphology), solvent screening, kinetics, heat of reaction, separations, solvent exchange, phase separations and the like.

Appropriate analytical techniques for use by research system 100 include, for example, infrared thermography, chromatography (gas or liquid), capillary electrophoresis, mass spectrometry, optical reflection or transmission, viscometry, mechanical resonators, solubility, differential scanning calorimetry, elongation, indentation, deformation, or imaging or spectroscopy with any wavelength in the electromagnetic spectrum (x-ray, infrared, ultraviolet, visible, ultrasonic or microwave). In one implementation, process database 260 and inventory database 250 are cross-referenced to provide design rules correlating particular chemicals, materials, etc., in inventory database 250 with particular processes, instruments/equipment, or analytical techniques suited for those materials in process database 260 (or, of course, vice versa).

Users access user interface subsystem 220 through remote user interface program 150 running on user's computer system 130 (which can be a stand-alone experiment design tool program, or a client program such as a web browser configured to access an experiment design tool program running on research system 100) and remotely design experiments to be executed by research system 100. In one implementation, user interface subsystem 220 controls the remote user interface program in a server/client relationship, providing that program with access to information in inventory database 250 and process database 260 concerning the availability of particular materials and experimental methods in a user's experiment design. Optionally, remote user interface program 150 and/or user interface subsystem 220 can be configured to restrict the user's access to information in databases 250, 260 (and 270) based on user-specific business rules (for example, rules based on or stored as customer information in customer database 240). Such rules can be configured by the user, the user's organization, or the operator of research system 100 to limit or focus the user's ability to design experiments to match the user's business. Thus, for example, if a user designing a set of experiments specifies a particular screening method from process database 260, user interface subsystem 220 will respond with a choice of materials from inventory database 250 that are identified by the stored design rules as suitable for characterization by that screening method; conversely, if the user selects a particular chemical or material from inventory database 250, user interface subsystem 220 will invoke the applicable design rules to respond with a choice of experimental procedures or screening methods from process database 260 that research system 100 is configured to perform using that material. Likewise, if the user's customer information identifies the user's business as specialty polymers, user interface 220 can limit the user's design choices to materials and methods appropriate for experiments in that field. Optionally, in these implementations remote user interface program 150 can be configured to permit the user to search inventory database 250 and process database 260 to retrieve information about what materials and methods can be incorporated into experiment designs for execution by research system 100. In other implementations, design rules based on information in inventory database 250 and process database 260 can be incorporated directly into remote user interface program 150, such that an open connection with user interface subsystem 220 is not required during experiment design. User interface subsystem 220 receives an experiment request embodying the user's experiment design and passes the request to research engine 230 and laboratory personnel for evaluation. Optionally, user interface subsystem 220 also provides a user interface through which a user can monitor the progress of the experiments, such as a search program for searching and analyzing experimental data stored in an experiment database 270.

Research engine 230 uses information from customer database 240, inventory database 250, process database 260 and user interface subsystem 220, in combination with input from laboratory personnel employed by the operator of research system 100, to generate an experimental plan for execution of a user-designed set of experiments on research system 100. Research engine 230 controls the preparation and execution of a set of experiments, and provides experimental results to experiment database 270 and to the user's computer system for analysis.

Figure 3:
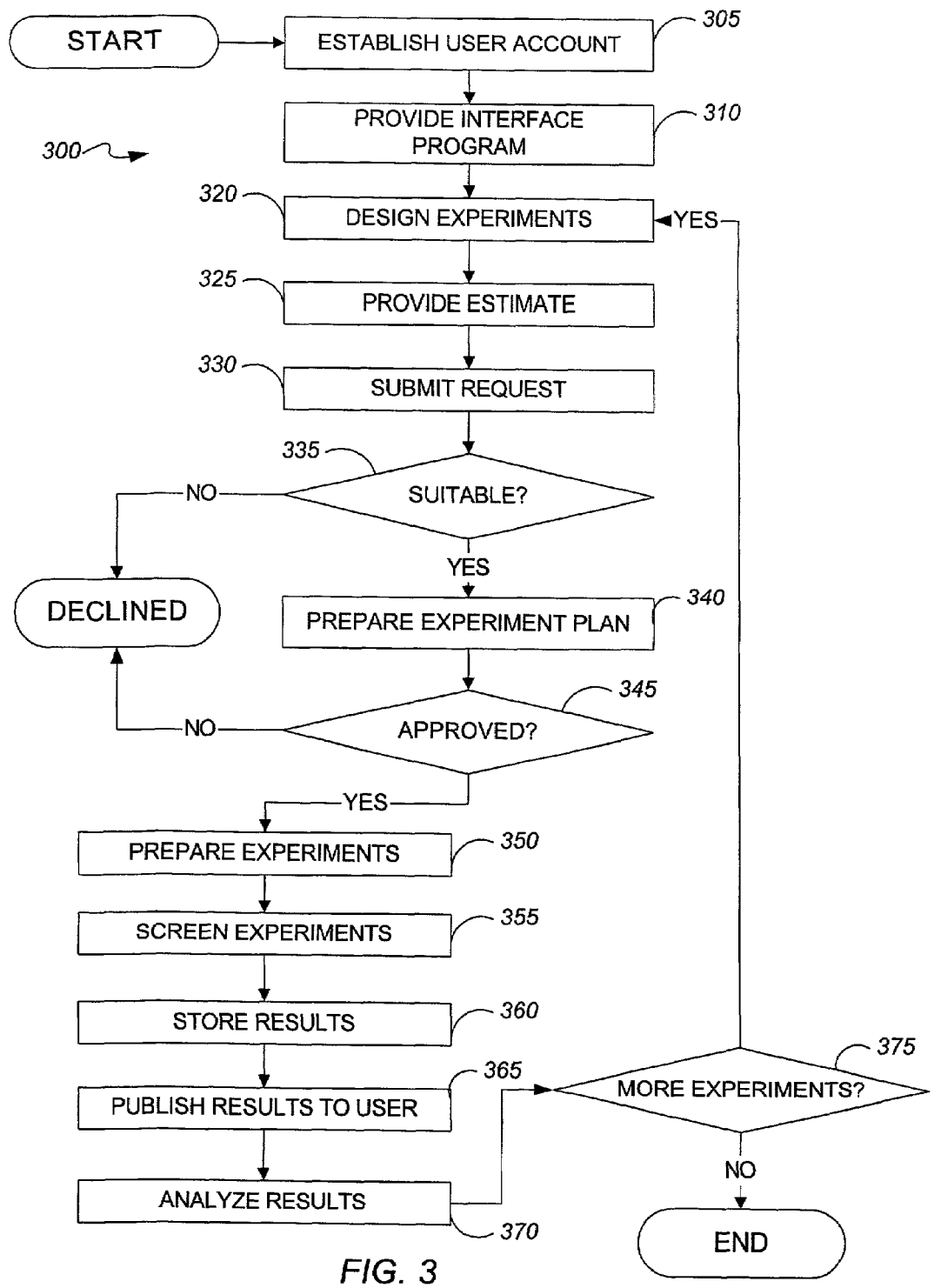
FIG. 3 is a flow diagram illustrating a method performed using the research system of the present invention.

The general method 300 performed using research system 100 is illustrated in FIG. 3. Optionally, a user begins by establishing an account within research system 100 (step 305), providing information through user interface subsystem 220 that customer information subsystem 200 uses to establish a customer record for the user in customer database 240. Authorized users receive access to a remote user interface program 150 (step 310), which can be a stand alone application or a client application such as a web browser. After receiving access to remote user interface program 150, the user designs a set of experiments (step 320). As used in this specification, a "set of experiments" refers to one or more experimental procedures to be performed in part or in their entirety using high-throughput technologies. "High-throughput technologies," in turn, refers to techniques, methodologies, processes, synthetic routes or instrumentation useful for the simultaneous, parallel or rapid serial: (i) synthesis, (ii) processing, (iii) analysis, or (iv) characterization of multiple compounds, compositions, materials or mixtures either on a substrate, in a parallel reactor, container or mixing system, or in a time that is rapid in comparison to a time frame that is traditional for the transformation to be performed. In some implementations, application of high-throughput screening methods can provide screening results for more than 10, 25, 48, 96, 192 or 225 compounds, compositions materials or mixtures in times less 48 hours, 36 hours, 24 hours, 12 hours, 6 hours, 60 minutes, 30 minutes or even 15 minutes depending on the particular chemistry and screening method involved. In a preferred implementation, the set of experiments includes at least 25 experiments; in more preferred implementations, the set of experiments includes more than 50, 100, 200, 500, 1000, 2500, 5000 or even 10,000 or 25,000 experiments.

To design a set of experiments, the user designs a library of materials, which, as used in this specification, refers to a matrix having two or more elements or members, generally containing some variance in chemical or material composition, amount, reaction conditions, and/or processing conditions, where an element represents a single constituent, location or member in a library containing one set of chemicals or materials subject to one set of reaction or processing conditions. The user specifies one or more starting materials from inventory database 250 and defines one or more distribution patterns to be used to distribute the specified materials to locations in the library of materials. The user can also define one or more processing conditions or parameters to be used in preparation of the library of materials or applied to the prepared library, and one or more screening methods from process database 260 that research system 100 will apply to the library of materials to generate experimental results. Optionally, the user is provided with an estimate of the time and/or cost of performing the set of experiments defined by the experiment design (step 325), either from general process information incorporated in remote user interface program 150 or from more detailed information on the price of particular materials and methods and the time required to perform those methods retrieved from inventory database 250 and process database 260.

The user submits the completed design as an experiment request to research system 100 through user interface subsystem 220 (step 330). Upon receipt of an experiment request by research system 100, the design embodied in the experiment request is evaluated (by research engine 230 based on information in inventory database 250 and process database 260, or manually by laboratory personnel employed by the operator of research system 100, or by a combination of manual and automated analysis) to determine whether the set of experiments is suitable for execution by research system 100 (step 335). Preferably, this evaluation includes, for example, consideration of safety and supply issues, issues relating to the appropriateness of specified materials and analytic methods, and, of course, time and cost; the evaluation can also include consultation with the user to determine whether modifications to the experiment design are appropriate or desirable. If it is determined that the experiment request is unsuitable—for example, if the set of experiments embodied in the experiment request would be unreasonably hazardous or if particular synthetic or screening instruments 265 that would be required are unavailable—research system 100 declines the experiment request (the NO branch of step 335), informing the user through user interface 150 that the request cannot be fulfilled. If it is determined that the experiment request is suitable for execution by research system 100 (the YES branch of step 335), research engine 230 uses the experiment design and information from inventory database 250 to prepare an experimental plan detailing the materials and methods that research system 100 will use to execute the set of experiments (step 340), including, for example, specific amounts of materials and prices for materials and methods to be used, and information on specific analytical methods and analysis to be applied in screening, including standards and references for comparison. User interface subsystem 220 communicates the experimental plan to the user for review and approval (step 345). If the user does not approve of the experimental plan (the NO branch of step 345), he or she communicates her disapproval through user interface subsystem 220 and the experiment request is declined.

If the user approves (the YES branch of step 345), research engine 230 prepares the specified library of materials according to the experiment design (as modified by any subsequent consultation), applying any specified process conditions to the members of the library of materials (step 350). Research engine 230 then carries out the specified screening method or methods (step 355) using automated screening instruments 265 and generates a set of experimental data reflecting the results of the screen(s). The resulting data is stored in experiment database 270 (step 360), and is communicated to the user using user interface subsystem 220 (step 365), for example, in the form of an "experimental workbook" page or pages (in electronic and/or hard copy form) detailing the experimental conditions and results. By executing the set of experiments using high throughput technologies, research system 100 can provide experimental results to the user far more quickly than using conventional research methods. For example, in a preferred implementation, the user receives experimental results from execution of the set of experiments within in a number of days after approval of the experimental plan equal to the number of experiments divided by 5. In more preferred implementations, experimental results are provided in a number of days after approval of the experimental plan equal to the number of experiments divided by 10, 20, 50 or even 100 depending on the complexity of the experiments and the precise screening method or methods selected.

The user is then free to analyze the experimental results on his or her own computer system 130 (step 370); user interface subsystem 220 can be configured to provide the user with access to the experiment database for this purpose as well. Optionally, after the user has analyzed the experimental results, remote user interface program 150 allows the user to submit a request to the operator of research system 100 to purchase materials yielding favorable results. Thus, for example, where the set of experiments is directed to identifying promising target compounds, research system 100 can provide the user with means to purchase particular target compounds identified during execution of the set of experiments. Likewise, where the set of experiments is directed to optimization of a chemical process such as synthesis of pharmaceutically active compounds, research system 100 can provide the user with means to purchase promising intermediates identified during execution of the set of experiments.

Optionally, after analyzing the experimental results, the user can use remote user interface program 150 and user interface subsystem 220 to define additional experiments based on the experimental results (step 375). In one implementation, the user's initial experiment request incorporates only a partial experiment design (e.g., a design that defines only a portion of a library of materials); likewise, the user can select only a subset of the experiment design for initial execution. After receiving and analyzing experimental results from execution by research system 100 of that partial experiment design, the user can complete the experiment design, taking the preliminary results from the partial design into consideration. In this way, the user can use experimental results from a limited number of experiments to define an optimum set of experiments to be executed by research system 100.

As mentioned above, the user registers with research system 100 and establishes an account in step 305. When the user accesses user interface subsystem 220—for example, by connecting the user's client system 130 to a server running research system program 120 over an internet connection, accessing a web site maintained by research system 100 or dialing in to a server running research system program 120—user interface subsystem 220 determines whether the user has previously accessed research system 100, for example by detecting a cookie on the user's computer system 130 or by searching customer database 240 for a customer record for the user. If the user has not previously accessed research system 100, user interface subsystem 220 prompts the user to provide identifying customer information, including a user name, password and contact information as described above. Customer information subsystem 200 adds a new customer record to customer database 240 and, in world wide web implementations, places a cookie on the user's computer system 130. For users who have previously registered with research system 100, user interface subsystem 220 prompts the user to enter a user name and password, and verifies that information against the corresponding customer record in customer database 240 before allowing the user to proceed.

Once the user has accessed research system 100, the user designs a set of experiments using a remote user interface program 150 such as those disclosed in co-pending and commonly assigned U.S. patent application Ser. No. 09/420,334, filed Oct. 18, 1999, which is hereby incorporated by reference. Remote user interface program 150 provides a graphical user interface through which the user can search the inventory database 250 and process database 260 for materials and experimental methods of interest and use these materials and methods to define a set of experiments at a conceptual level, including identifying particular reactions, materials, reactors, process conditions, and/or analytical tools to be used. The user can use remote user interface program 150 to access a search function, implemented by user interface subsystem 220 with conventional database tools, that identifies items in the inventory and process databases that match search criteria (e.g., material name, property, characteristic, or category, chemistry or analytical method) specified by the user. The user can use this information to define a set of design elements corresponding to a design workspace, one or more mappings or distribution schemes for assigning materials to individual members of a library of materials, and one or more process parameters to be applied to one or more library members, and to apply a set of stored design rules to define a high level library design.

Figure 4:
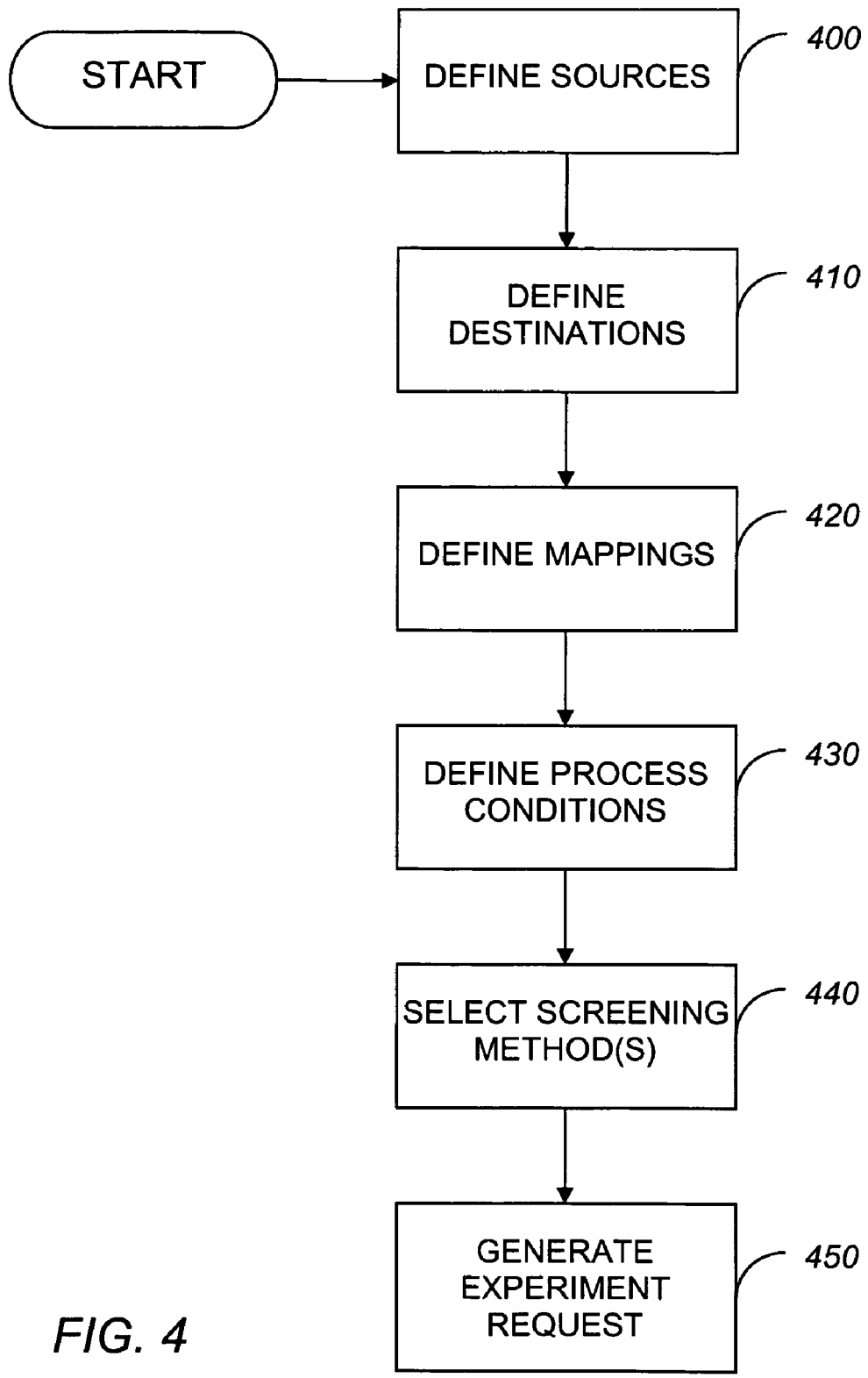
FIG. 4 is a flow diagram illustrating a method of designing a set of experiments that can be executed with the research system of the present invention.

A method of designing a set of experiments with remote user interface program 150 is illustrated in FIG. 4. The user defines a workspace by defining one or more sources (step 400) and one or more destinations (step 410). As used in this specification, a source is a starting material, such as a chemical or mixture of chemicals, which will be used as a component in creating a library, while a destination is a conceptual arrangement of elements (e.g., a matrix) representing the library. Although a destination can represent a physical substrate in or on which a library is to be created, it is not constrained to represent an actual physical substrate and can correspond to a conceptual library environment.

In one implementation, remote user interface program 150 is configured to provide the user with a list of available sources (e.g., materials in inventory 255) from which to design experiments for execution by research system 100. The list of sources can be context sensitive—for example, limited according to stored design rules based on customer information or particular selections made during the design process. That is, if the user selects a particular material, remote user interface program 150 can call stored design rules to permit selection of additional sources only from a list of materials in inventory 255 that are compatible with the selected material; alternatively, if the user selects a particular type of experiment or a particular screening method, remote user interface program 150 can permit the user to select only those sources deemed appropriate for the particular chemistry or screen involved. If desired, remote user interface program 150 and/or user interface subsystem 220 can be configured to suggest appropriate sources based on stored design rules and information input by the user. In other implementations, remote user interface program 150 can permit the user to define "custom" sources corresponding, for example, to materials the user will provide to the laboratory operating research system 100 for use in a set of experiments. In these implementations, the experiment design can also include additional information about such custom sources, including information relating to chemical reactivity, safety and the like, that will be required for laboratory personnel to evaluate the experiment request in step 335.

The user then creates a distribution scheme assigning component materials from sources to destination regions to define the composition of each element of an experimental matrix (step 420), for example, by providing a gradient or other mathematical relationship defining how the material is to be distributed across the matrix of library members. The user can incorporate process conditions into the experiment design by defining one or more parameters specifying conditions, including both constant conditions to be applied to all or a subset of matrix elements (i.e., the set (or a subset) of experiments) or varying conditions across one or more elements of the experimental matrix (step 430). Such parameters can include any external conditions, such as temperature, pressure, mixing speed, quench time, flow rate and the like. Again, remote user interface program 150 and/or user interface subsystem 220 can be configured to suggest appropriate distribution schemes or process conditions based on information input by the user.

Similarly, the user can identify one or more high-throughput screening techniques to be applied to all or a subset of the experimental matrix (step 440). In one implementation, remote user interface program 150 is configured to permit the user to select from a list of available high-throughput reactions and/or screens implemented by instruments 265, such as those disclosed in U.S. patent application Ser. No. 09/093,870, filed Jun. 9, 1998, now issued as U.S. Pat. No. 6,149,882; U.S. patent application Ser. No. 09/300,634, filed Apr. 27, 1999, now issued as U.S. Pat. No. 6,395,552; U.S. patent application Ser. No. 09/039,991, filed Mar. 16, 1998, now issued as U.S. Pat. No. 6,087,181; U.S. patent application Ser. No. 09/067,448, filed Apr. 27, 1998; U.S. patent application Ser. No. 09/227,558, filed Jan. 8, 1999, now issued as U.S. Pat. No. 6,720,186; U.S. patent application Ser. No. 09/285,363, filed Apr. 2, 1999; U.S. patent application Ser. No. 09/285,393, filed Apr. 2, 1999, now issued as U.S. Pat. No. 6,265,226; U.S. patent application Ser. No. 09/285,333, filed Apr. 2, 1999, now issued as U.S. Pat. No. 6,260,407; U.S. patent application Ser. No. 09/285,335, filed Apr. 2, 1999, now issued as U.S. Pat. No. 6,175,409; U.S. patent application Ser. No. 09/285,392, filed Apr. 2, 1999, now issued as U.S. Pat. No. 6,294,388; U.S. patent application Ser. No. 09/410,546, filed Oct. 1, 1999, now issued as U.S. Pat. No. 6,296,771; U.S. patent application Ser. No. 09/414,744, filed Oct. 8, 1999, now issued as U.S. Pat. No. 6,536,944; U.S. patent application Ser. No. 08/946,135, filed Oct. 7, 1997, now issued as U.S. Pat. No. 6,541,271; U.S. Pat. No. 5,959,297; U.S. Pat. No. 5,985,356; U.S. Pat. No. 6,030,917; U.S. Pat. No. 6,034,775; U.S. patent application Ser. No. 09/033,207, filed Mar. 2, 1998; U.S. patent application Ser. No. 09/174,986, filed Oct. 19, 1998, now issued as U.S. Pat. No. 6,157,499; U.S. patent application Ser. No. 09/417,125, filed Nov. 19, 1998, now issued as U.S. Pat. No. 6,528,026; U.S. patent application Ser. No. 09/177,170, filed Oct. 22, 1998, now issued as U.S. Pat. No. 6,548,026; U.S. patent application Ser. No. 09/211,982, filed Dec. 14, 1998, now issued as U.S. Pat. No. 6,306,658; U.S. patent application Ser. No. 09/239,223, filed Jan. 29, 1999, now issued as U.S. Pat. No. 6,489,168; U.S. patent application Ser. No. 09/474,344, filed Dec. 29, 1999, now issued as U.S. Pat. No. 6,373,570; U.S. patent application Ser. No. 09/112,247, filed Jul. 8, 1998, now issued as U.S. Pat. No. 6,151,123; U.S. patent application Ser. No. 09/149,586, filed Sep. 8, 1998, now issued as U.S. Pat. No. 6,410,332; U.S. patent application Ser. No. 09/458,398, filed Dec. 10, 1999, now issued as U.S. Pat. No. 6,535,824; U.S. patent application Ser. No. 09/215,417, filed Dec. 18, 1998; U.S. patent application Ser. No. 09/205,071, filed Dec. 4, 1998, now issued as U.S. Pat. No. 6,485,692; U.S. patent application Ser. No. 09/518,794, filed Mar. 3, 2000, now issued as U.S. Pat. No. 6,749,814; U.S. Provisional Patent Application No. 60/157,338, filed Oct. 1, 1999; and WO 97/32208. Each of these patents and patent applications is incorporated herein by reference.

As described above, in this implementation, remote user interface program 150 can be configured to call stored design rules limiting the user's choice of screening method to those available high-throughput screens that are deemed useful for or compatible with the chemistry embodied in the user's experiment design. Here, too, remote user interface program 150 and/or user interface subsystem 220 can be configured to suggest appropriate screening techniques based on design rules and information input by the user. In other implementations, remote user interface program 150 can permit the user to identify user-defined "custom" screens to be used by research system 100 in executing the experiment design. In these implementations, the experiment design can also include additional information about such custom screens, including information relating to screening protocols, data processing, safety and the like, that will be required to allow laboratory personnel to evaluate the experiment request in step 335.

Based on the user's library design, remote user interface program 130 creates a set of material handling instructions, which can take the form of a data file or "recipe file" that can be implemented by automated synthesis instruments controlled by research engine 230, as described in co-pending U.S. patent application Ser. No. 09/305,830, filed on May 5, 1999, now issued as U.S. Pat. No. 6,507,945, which is incorporated by reference herein. Remote user interface program 150 packages this recipe file with the user's specified screening information selecting one or more high-throughput screening methods to form an experiment request (step 450). Remote user interface program 150 also calculates an initial estimate of the cost of the set of experiments defined by the experiment request and the time that research system 100 would require to execute the set of experiments. The user can then send the request to user interface subsystem 220 in step 330 above.

Upon receipt of an experiment request by user interface subsystem 220, research system 100 begins tracking the status of the user's request. Customer information subsystem 200 and research engine 230 store information relating to the experiment request in customer database 240 and experiment database 270. Research system 100 then initiates an evaluation of the request in step 335 above. Research engine 230 and/or laboratory personnel assess the compatibility of the experiment design with existing and available instrumentation and chemistry capability to determine whether the request is suitable for execution by research system 100 as described above. Research system 100 produces a refined estimate of cost and scheduling as well. As also discussed above, research system 100 also provides for the optional exchange of information between the user and laboratory personnel, allowing for the use of custom materials and the development and validation of custom methods, which research system 100 adds to the appropriate databases for future use.

After the assessment of the suitability of the experiment design, research engine 230 prepares an experimental plan in step 340. Based on the general type of library or other information specified in the design (for example, the categories of materials used in the library, the chemistry involved in the experiments, and/or the screening required), research engine 230 retrieves an appropriate experimental plan template from process database 260 and completes the template with information relating to specific materials, parameters and experimental methods from the experiment design. The resulting experimental plan includes detailed documentation of the processes and standards to be used in carrying out the set of experiments, as well as the type of output to be generated, an experimental timeline and specific service and consumable costs for executing the experiment design. Research system 100 provides the user with access to the plan in step 345 through an experimental plan viewer implemented by user interface subsystem 220 (which can include software incorporated in remote user interface program 150 running on the user's computer system 130). This viewer permits the user to view and print the experimental plan, to provide additional comments about the plan and to either approve or decline the plan, and transmits this information back through user interface 220 to research system 100, where it is stored in customer database 240 and experiment database 270.

Once the user has approved the experimental plan, research engine 230 executes the plan in steps 350 and 355. Using combinatorial synthesis techniques and automated process control systems, such as those disclosed in the patents and patent applications referred to above, as well as U.S. patent application Ser. No. 08/941,170, filed Sep. 30, 1997, now issued as U.S. Pat. No. 6,468,806; U.S. patent application Ser. No. 09/156,827, filed Sep. 18, 1998; U.S. patent application Ser. No. 08/841,423, filed Apr. 22, 1997, now issued as U.S. Pat. No. 6,045,671; and U.S. patent application Ser. No. 09/237,502, filed Jan. 26, 1999, now issued as U.S. Pat. No. 6,364,956, each of which is incorporated by reference herein, research engine 230 prepares a library of materials specified by the experimental matrix defined in the experiment design. Optionally, the process can be fully automated, with research engine 230 retrieving the specified starting materials from inventory 255 using inventory subsystem 210; alternatively, laboratory personnel can retrieve the appropriate starting materials from inventory 255 for use by research engine 230 and automated synthesis instruments 265. Research engine 230 applies the specified process conditions and screens the set of experiments, using high throughput screening techniques and instruments 265 such as those disclosed in the patents and patent applications referred to and incorporated by reference above. By using high throughput technologies to prepare and screen the libraries, research engine 230 can provide experimental results in significantly less time than conventional research methods.

In step 360, research engine 230 stores the experimental results in experiment database 270. Research system 100 provides these results to the user in step 365 through an experimental workbook viewer implemented by user interface subsystem 220 (which can include software incorporated in remote user interface program 150 running on the user's computer system 130). This viewer provides for comprehensive examination and printing of the experimental data and permits the user to download the data to the user's computer system 130 for further analysis.

For repeat users, research system 100 can provide additional data management capabilities through a graphical data explorer program implemented by user interface subsystem 220 (either incorporated in remote user interface program 150 or remotely accessed by client software running on the user's computer system 130). The data explorer program provides the user with the ability to search and manipulate data from multiple experiments stored in experiment database 270 maintained by the operator of research system 100. Using the data explorer program, the user can access a search function implemented by user interface subsystem 220 with conventional database tools that permits the user to construct search queries to interrogate the experiment database based on simple experimental variables such as library design, composition or processing conditions, analytical or screening methods or measured or calculated properties, or on more complex relationships such as experimental trends or series. In one implementation, the data explorer program accesses only data stored in an experiment database 270 corresponding to experiments requested by a single user or institution, which both relieves the user or institution from the burden of creating and maintaining its own database and maintains the security of the user's or institution's experimental data. Alternatively, the data explorer program can provide users with access to experimental results from a broader range of experiments in one or more experiment databases 270—for example, a user can purchase the right to access an aggregate database for a fee or by agreeing to submit the user's own results to the aggregate database.

Research system 100 can include features of conventional web pages. For example, user interface 220 can generate and display advertising banners for products or services available from the operator of research system 100. Research system 100 can also provide text, voice or video links between users and the operator of research system 100 through user interface subsystem 220 to facilitate experiment design, approval and execution, as well as the provision and analysis of experimental results.

Research system 100 can be implemented in digital electronic circuitry, or in computer hardware, firmware, software, or in combinations of them. Each computer program can be implemented in a high-level procedural or object-oriented programming language, or in assembly or machine language if desired; and in any case, the language can be a compiled or interpreted language. Suitable processors include, by way of example, both general and special purpose microprocessors. Generally, a processor will receive instructions and data from a read-only memory and/or a random access memory. Generally, a computer will include one or more mass storage devices for storing data files; such devices include magnetic disks, such as internal hard disks and removable disks; magneto-optical disks; and optical disks. Storage devices suitable for tangibly embodying computer program instructions and data include all forms of non-volatile memory, including by way of example semiconductor memory devices, such as EPROM, EPROM, and flash memory devices; magnetic disks such as internal hard disks and removable disks; magneto-optical disks; and CD-ROM disks.

A number of embodiments of the invention have been described. Nevertheless, it will be understood that various modifications may be made without departing from the spirit and scope of the invention. For example, user information, including customer information and experiment requests, and experimental results can be communicated electronically by facsimile or voice telephony, Internet, Intranet, or internal computer network, or in printed form. Accordingly, other embodiments are within the scope of the following claims.

What is claimed is:

1. A method for carrying out a set of experiments, the method comprising:

providing to a remote user at a first location a computer-implemented experiment design tool for generating an experiment request for execution of a set of experiments, the experiment request including electronic data embodying an experiment design defining a set of experiments, the experiment design including electronic data defining an experiment matrix having a plurality of matrix elements, one or more starting materials assigned to the matrix elements and one or more process conditions to be applied to the matrix elements, each of a plurality of matrix elements being defined by a unique combination of starting materials and/or process conditions, the experiment design also including electronic data defining a screening method to be applied to generate experimental results;

receiving at a second location a first experiment request for a set of experiments to be performed at the second location, the request including a first experiment design generated by the experiment design tool, the first experiment design defining a first experiment matrix having a first plurality of matrix elements, a first set of one or more starting materials, and a first set of one or more process conditions, the first experiment design also defining a first screening method, the second location being remote from the first location;

preparing a first library of materials at the second location according to the first experiment design, the first library of materials corresponding to the first experiment matrix, the first library of materials having a plurality of members corresponding to elements of the first experiment matrix, the plurality of members containing a plurality of actual compounds, compositions, materials or mixtures;

applying the first set of process conditions to the members of the first library of materials at the second location to transform at least one of the starting materials into at least one product;

applying the first screening method to the members of the first library of materials at the second location to generate experimental results; and providing electronic data describing the experimental results to the remote user at the first location.

2. The method of claim 1, wherein:
the first screening method is a high throughput screening method.

3. The method of claim 2, wherein:
the first screening method is selected from the group consisting of infrared thermography, chromatography, capillary electrophoresis, mass spectrometry, optical reflection, optical transmission, viscometry, mechanical resonators, solubility, differential scanning calorimetry, elongation, indentation, deformation or spectroscopy.

4. The method of claim 1, wherein:
the first experiment matrix includes at least 50 elements; and
the experimental results are provided to the user within 20 days from preparation of the first library.

5. The method of claim 1, wherein:
the first experiment matrix includes at least 96 elements; and
the experimental results are provided to the user within 10 days from preparation of the first library.

6. The method of claim 1, wherein:
the first experiment matrix includes at least 1000 elements; and
the experimental results are provided to the user within 50 days from preparation of the first library.

7. The method of claim 1, wherein:
the first experiment matrix includes at least 1000 elements; and
the experimental results are provided to the user within 20 days from preparation of the first library.

8. The method of claim 1, wherein:
the first experiment matrix includes at least 1000 elements; and
the experimental results are provided to the user within 10 days from preparation of the first library.

9. The method of claim 2, further comprising:
in response to providing the experimental results, receiving a second experiment design defining one or more additional experiments;
preparing a second library of materials based on the second experiment design;
applying one or more process conditions specified in the second experiment design to the members of the second library of materials to transform at least one of the starting materials into a product and applying a second screening method to generate additional experimental results; and
providing the additional experimental results to the remote user.

10. The method of claim 9, wherein:
the second library of materials is a superset of the first library of materials.

11. The method of claim 9, wherein:
the second screening method and the first screening method are different.

12. The method of claim 2, wherein:
the computer-implemented experiment design tool includes an interactive user interface configured to enable the remote user to select materials from a list of materials in a remote material inventory.

13. The method of claim 2, wherein:
the computer-implemented experiment design tool includes an interactive user interface configured to enable the user to select processing conditions from a list of processing conditions that can be implemented by a remote process control system.

14. The method of claim 2, wherein:
the computer-implemented experiment design tool includes an interactive user interface configured to enable the user to select high throughput screening methods from a list of screening methods that can be performed by one or more screening instruments available at a remote laboratory location.

15. The method of claim 2, wherein:
the computer-implemented experiment design tool includes an interactive user interface configured to access one or more databases of available materials, process conditions and high throughput screening methods.

16. The method of claim 2, wherein:
the first screening method is automatically defined based on one or more of the starting materials and process conditions.

17. The method of claim 2, further comprising:
evaluating the first experiment design before preparing the first library of materials to generate an experimental plan including electronic data describing a proposed execution of the set of experiments;
providing the experimental plan to the remote user; and
receiving an input from the user in response to the experimental plan, wherein the preparing the library of materials, the applying the process conditions, the applying the screening method, and the providing the experimental results are only performed when the user approves of the experimental plan.

18. The method of claim 17, wherein:
evaluating the first experiment design includes generating an estimate of time and/or cost to perform the set of experiments defined by the first experiment design.

19. The method of claim 17, wherein:
evaluating the first experiment design includes determining whether the design conforms to a set of experiment parameters, and, if not, communicating to the remote user that one or more experiments defined by the experiment design cannot be executed.

20. The method of clam 19, wherein;
determining whether the design conforms to the set of experiment parameters includes determining whether the assigned starting materials specified in the first experiment design are present in an inventory of materials.

21. The method of claim 19, wherein:
evaluating the first experiment design includes determining whether the assigned starting materials have chemical or physical properties falling within a predetermined set of chemical or physical properties.

22. The method of claim 1 wherein:
the first experiment request is received from the remote user over a computer network.

23. The method of claim 1, wherein:
the first experiment design includes information identifying one or more custom materials assigned to one or more matrix elements; the method further comprising:
receiving the custom materials from the remote user for use in preparing the library of materials.

24. The method of claim 1, wherein:
the first experiment design defines a set of experiments directed to chemicatalysis or biocatalysis.

25. The method of claim 1, wherein:
the first experiment design defines a set of experiments directed to optimization of a chemical synthetic process.

26. The method of claim 25, wherein:
the set of experiments is directed to the preparation of pharmaceutical products or intermediates.

27. The method of claim 25, wherein:
the set of experiments is directed to the preparation of fine chemicals.

28. The method of claim 25, wherein:
the set of experiments is directed to the preparation of specialty chemicals.

29. The method of claim 25, wherein:
the set of experiments is directed to the preparation of commodity chemicals.

30. The method of claim 1, wherein:
the first experiment design defines a set of experiments directed to polymerization.

31. The method of claim 30, wherein:
the set of experiments is directed to the preparation of polymeric coatings, adhesives, dispersants, surfactants or additives.

32. The method of claim 1, wherein:
the first experiment design defines a set of experiments directed to the preparation of electronic materials.

33. The method of claim 1, wherein:
the experiment design defines a set of experiments directed to the preparation of composites or alloys.

34. The method of claim 2, wherein:
the user receives the experimental results by accessing a results database through a remote computer-implemented interactive user interface.

35. The method of claim 2, further comprising:
in response to providing the experimental results, receiving from the remote user a request to purchase a starting material or product corresponding to one of the elements of the experiment matrix.

36. The method of claim 1, wherein:
the experiment design tool is provided as a computer program to be executed by a computer system at the first location.

37. The method of claim 1, wherein:
the experiment design tool is provided as a computer program executed by a server process running at the second location; and
the remote user accesses the experiment design tool using a client process running at the first location.

38. A computer-implemented method for obtaining experimental results for a set of experiments, the method comprising:
generating at a first location an experiment request for execution of a set of experiments, the experiment request including electronic data embodying an experiment design defining a set of experiments, the experiment design including an experiment matrix having a plurality of elements, one or more starting materials assigned to the matrix elements, and one or more process conditions to be applied to the matrix elements, each of a plurality of matrix elements being defined by a unique combination of starting materials and/or process conditions, the experiment design also defining a screening method to be applied to generate experimental results;
communicating the experiment request to a laboratory at a second location for execution, the second location being remote from the first location; and
receiving at the first location experimental results obtained at the laboratory by applying the process conditions to a library of materials corresponding to the experiment matrix to transform at least one of the starting materials into at least one product and applying the specified screening method.

39. The method of claim 38, wherein:
generating an experiment request includes selecting one or more starting materials from a list of materials in a remote material inventory.

40. The method of claim 38, wherein:
generating an experiment request includes selecting one or more processing conditions from a list of processing conditions that can be implemented by a remote process control system.

41. The method of claim 38, wherein:
generating an experiment request includes selecting a screening method from a list of screening methods that can be performed by one or more remote screening instruments.

42. The method of claim 38, wherein:
the screening method is automatically defined based on a selection of one or more of the starting materials and process conditions.

43. The method of claim 38, wherein:
the experiment request is communicated to the laboratory over a computer network.

44. The method of claim 38, further comprising:
receiving at the first location an experimental plan describing a proposed execution of the set of experiments; and
if the proposed execution of the set of experiments is acceptable, communicating an approval of the experimental plan to the laboratory.

45. The method of claim 44, wherein:
the experimental plan includes an estimate of time and/or cost to perform the set of experiments.

46. The method of claim 44, wherein:
the experimental plan includes an indication whether the design conforms to a set of experiment parameters.

47. The method of clam 44, wherein:
the experimental plan includes an indication whether the assigned starting materials specified in the first experiment design are present in an inventory of materials.

48. The method of claim 44, wherein:
the experimental plan includes an indication whether the assigned starting materials have chemical or physical properties falling within a predetermined set of chemical or physical properties.

49. The method of claim 38, further comprising:
in response to receiving the experimental results, generating a second experiment design defining one or more additional experiments;
communicating the second experiment design to the laboratory at the second location for execution; and receiving at the first location additional experimental results obtained at the laboratory by execution of the additional experiments according to the second experiment design.

50. The method of claim 38, wherein:
receiving the experimental results includes accessing a results database through a remote computer-implemented interactive user interface.

51. A computer-readable storage medium tangibly embodying a research system program, the program comprising instructions operable to cause a programmable processor to:
provide to a remote user at a first location a computer-implemented experiment design tool for generating an experiment request for execution of a set of experiments, the experiment request including electronic data embodying an experiment design defining a set of experiments, the experiment design including an experiment matrix having a plurality of matrix elements, one or more starting materials assigned to the matrix elements and one or more process conditions to be applied to the matrix elements, each of a plurality of matrix elements being defined by a unique combination of starting materials and/or process conditions, the experiment design also defining a screening method to be applied to generate experimental results;
receive at a second location a first experiment request for a set of experiments to be performed at the second location, the request including an experiment design generated by the experiment design tool, the second location being remote from the first location;
direct an automated synthesis instrument to prepare a library of materials corresponding to the experiment matrix, the library of materials having a plurality of members;
direct an automated instrument to apply the process conditions to the members of the library of materials to transform at least one of the starting materials into at least one product;
direct an automated screening instrument to apply a first screening method defined by the first experiment design to generate experimental results; and
provide the experimental results to the remote user.

52. The computer-readable storage medium of claim 51, further comprising instructions operable to cause a programmable processor to:
in response to providing the experimental results, receive a second experiment design defining one or more additional experiments;
prepare a second library of materials based on the second experiment design;
apply one or more process conditions specified in the second experiment design to the members of the second library of materials to transform at least one of the starting materials into a product and apply a second screening method to generate additional experimental results; and
provide the additional experimental results to the remote user.

53. The computer-readable storage medium of claim 52, wherein:
the second library of materials is a superset of the first library of materials.

54. The computer-readable storage medium of claim 52, wherein:
the second screening method and the first screening method are different.

55. The computer-readable storage medium of claim 51, wherein:
the computer-implemented experiment design tool includes an interactive user interface configured to enable the remote user to select materials from a list of materials in a remote material inventory.

56. The computer-readable storage medium of claim 51, wherein:
the computer-implemented experiment design tool includes an interactive user interface configured to enable the user to select processing conditions from a list of processing conditions that can be implemented by a remote process control system.

57. The computer-readable storage medium of claim 51, wherein:
the computer-implemented experiment design tool includes an interactive user interface configured to enable the user to select high throughput screening methods from a list of screening methods that can be performed by one or more screening instuments available at a remote laboratory location.

58. The computer-readable storage medium of claim 51, wherein:
the computer-implemented experiment design tool includes an interactive user interface configured to access one or more databases of available materials, process conditions and high throughput screening methods.

59. The computer-readable storage medium of claim 51, wherein:
the first screening method is automatically defined based on one or more of the starting materials and process conditions.

60. The computer-readable storage medium of claim 51, further comprising instructions operable to cause a programmable processor to:
evaluate the first experiment design before preparing the library of materials to generate an experimental plan describing a proposed execution of the set of experiments; and
provide the experimental plan to the remote user.

61. The computer-readable storage medium of claim 51, wherein:
the experimental results are provided to the remote user in a results database accessible through a remote computer-implemented interactive user interface.

62. The computer-readable storage medium of claim 51, wherein:
the experiment design tool is provided as a computer program to be executed by a computer system at the first location.

63. The computer-readable storage medium of claim 51, wherein:
the experiment design tool is provided as a computer program executed by a server process running at the second location; and
the remote user accesses the experiment design tool using a client process running at the first location.

64. A computer-readable storage medium tangibly embodying a program for obtaining experimental results for a set of experiments, the program comprising instructions operable to cause a programmable processor to:
generate at a first location an experiment request for execution of a set of experiments, the experiment request including electronic data embodying an experiment design defining a set of experiments, the experiment design including an experiment matrix having a plurality of elements, one or more starting materials assigned to the matrix elements, and one or more process conditions to be applied to the matrix elements, each of a plurality of matrix elements being defined by a unique combination of starting materials and/or process conditions, the experiment design also defining a screening method to be applied to generate experimental results;

communicate the experiment request to a laboratory at a second location for execution, the second location being remote from the first location; and receive at the first location experimental results obtained at the laboratory by applying the process conditions to a library of materials corresponding to the experiment matrix to transform at least one of the starting materials into at least one product and applying the specified screening method.

65. The computer-readable storage medium of claim 64, further comprising instructions operable to cause a programmable processor to:

receive at the first location an experimental plan describing a proposed execution of the set of experiments; and in response to input indicating that the proposed execution of the set of experiments is acceptable, communicate an approval of the experimental plan to the laboratory.

66. The computer-readable storage medium of claim 65, wherein:

the experimental plan includes an estimate of time and/or cost to perform the set of experiments.

67. The computer-readable storage medium of claim 65, wherein:

the experimental plan includes an indication whether the design conforms to a set of experiment parameters.

68. The computer-readable storage medium of clam 65, wherein:

the experimental plan includes an indication whether the assigned starting materials specified in the first experiment design are present in an inventory of materials.

69. The computer-readable storage medium of claim 65, wherein:

the experimental plan includes an indication whether the assigned starting materials have chemical or physical properties falling within a predetermined set of chemical or physical properties.

70. The computer-readable storage medium of claim 64, further comprising instructions operable to cause a programmable processor to:

in response to receiving the experimental results, generate a second experiment design defining one or more additional experiments;

communicate the second experiment design to the laboratory at the second location for execution; and receive at the first location additional experimental results obtained at the laboratory by execution of the additional experiments according to the second experiment design.

71. The computer-readable storage medium of claim 65, wherein:

the experiment request is communicated to the laboratory over a computer network.

72. The computer-readable storage medium of claim 64, wherein:

the instructions operable to cause a programmable processor to generate an experiment request include instructions operable to cause a programmable processor to receive input selecting one or more starting materials from a list of materials in a remote material inventory.

73. The computer-readable storage medium of claim 64, wherein;

the instructions operable to cause a programmable processor to generate an experiment request include instructions operable to cause a programmable processor to receive input selecting one or more processing conditions from a list of processing conditions that can be implemented by a remote process control system.

74. The computer-readable storage medium of claim 64, wherein;

the instructions operable to cause a programmable processor to generate an experiment request include instructions operable to cause a programmable processor to receive input selecting a screening method from a list of screening methods that can be performed by one or more remote screening instruments.

75. The computer-readable storage medium of claim 64, wherein:

the screening method is automatically defined based on a selection of one or more of the starting materials and process conditions.

76. The computer-readable storage medium of claim 64, wherein:

the instructions operable to cause a programmable processor to receive the experimental results include instructions operable to cause a programmable processor to access a results database through a remote computer-implemented interactive user interface.

* * * * *